(12) United States Patent
Berenstein et al.

(10) Patent No.: US 7,695,488 B2
(45) Date of Patent: Apr. 13, 2010

(54) EXPANDABLE BODY CAVITY LINER DEVICE

(75) Inventors: Alejandro Berenstein, New York, NY (US); Joseph C. Eder, Los Altos Hills, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1102 days.

(21) Appl. No.: 10/107,689

(22) Filed: Mar. 27, 2002

(65) Prior Publication Data

US 2003/0187473 A1 Oct. 2, 2003

(51) Int. Cl.
*A61M 29/00* (2006.01)
(52) U.S. Cl. .................. 606/194; 606/191; 606/192; 606/195
(58) Field of Classification Search .......... 606/200, 606/192, 198, 199, 191, 194, 195; 623/1.11, 623/1.15, 1.2
See application file for complete search history.

(56) References Cited

U.S. PATENT DOCUMENTS

| | | | |
|---|---|---|---|
| 2,849,002 A * | 8/1958 | Oddo | 606/192 |
| 4,364,392 A | 12/1982 | Strother et al. | 128/325 |
| 4,705,517 A | 11/1987 | DiPisa, Jr. | 623/12 |
| 4,710,192 A | 12/1987 | Liotta et al. | 623/1 |
| 5,250,071 A | 10/1993 | Palermo | 606/198 |
| 5,334,210 A * | 8/1994 | Gianturco | 606/151 |
| 5,454,833 A | 10/1995 | Boussignac et al. | 606/213 |
| 5,522,822 A | 6/1996 | Phelps et al. | 606/151 |
| 5,522,836 A * | 6/1996 | Palermo | 606/200 |
| 5,534,024 A * | 7/1996 | Rogers et al. | 623/1.25 |
| 5,749,894 A * | 5/1998 | Engelson | 606/213 |
| 5,782,860 A | 7/1998 | Epstein et al. | 606/213 |
| 5,861,003 A | 1/1999 | Latson et al. | 606/213 |
| 5,899,917 A * | 5/1999 | Edwards et al. | 606/195 |
| 5,928,260 A | 7/1999 | Chin et al. | 606/200 |
| 5,935,148 A | 8/1999 | Villar et al. | 606/213 |
| 5,976,174 A | 11/1999 | Ruiz | 606/213 |
| 6,033,426 A | 3/2000 | Kaji | 606/213 |
| 6,036,720 A | 3/2000 | Abrams et al. | 606/213 |
| 6,063,070 A | 5/2000 | Eder | 606/1 |
| 6,063,104 A | 5/2000 | Villar et al. | 606/213 |
| 6,077,291 A | 6/2000 | Das | 606/213 |
| 6,086,577 A | 7/2000 | Ken et al. | 606/1 |
| 6,096,034 A | 8/2000 | Kupiecki et al. | 606/32 |
| 6,139,564 A | 10/2000 | Teoh | 606/213 |
| 6,168,570 B1 | 1/2001 | Ferrera | 600/585 |
| 6,168,592 B1 | 1/2001 | Kupiecki et al. | 606/32 |
| 6,168,615 B1 | 1/2001 | Ken et al. | 623/1 |
| 6,193,708 B1 | 2/2001 | Ken et al. | 606/1 |
| 6,238,403 B1 * | 5/2001 | Greene et al. | 606/108 |
| 6,293,960 B1 * | 9/2001 | Ken | 606/195 |
| 6,299,619 B1 * | 10/2001 | Greene et al. | 606/108 |
| 6,312,421 B1 | 11/2001 | Boock | 604/509 |
| 6,344,041 B1 | 2/2002 | Kupiecki et al. | 606/32 |

(Continued)

FOREIGN PATENT DOCUMENTS

EP 0 358 767 A1 1/1988

(Continued)

*Primary Examiner*—Darwin P Erezo
(74) *Attorney, Agent, or Firm*—Vista IP Law Group LLP

(57) ABSTRACT

The present invention is an aneurysm treatment device for treating aneurysms of various shapes and sizes.

24 Claims, 3 Drawing Sheets

U.S. PATENT DOCUMENTS

| | | | |
|---|---|---|---|
| 6,344,048 B1 | 2/2002 | Chin et al. | 606/200 |
| 6,346,117 B1 | 2/2002 | Greenhalgh | 606/200 |
| 6,375,668 B1 * | 4/2002 | Gifford et al. | 606/200 |
| 6,383,174 B1 | 5/2002 | Eder | 606/1 |
| 6,428,558 B1 | 8/2002 | Jones et al. | 606/200 |
| 6,454,780 B1 * | 9/2002 | Wallace | 606/151 |
| 6,511,468 B1 * | 1/2003 | Cragg et al. | 604/508 |
| 2003/0028209 A1 | 2/2003 | Toeh et al. | 606/191 |
| 2004/0098027 A1 * | 5/2004 | Teoh et al. | 606/200 |

FOREIGN PATENT DOCUMENTS

| | | |
|---|---|---|
| EP | 0 664 104 A2 | 7/1995 |
| EP | 0 711 532 A1 | 11/1995 |
| EP | 0 882 428 A2 | 12/1998 |
| WO | WO 94/06503 | 3/1994 |
| WO | WO 96/01591 | 2/1996 |
| WO | WO 97/26939 | 7/1997 |
| WO | WO 99/01591 | 1/1999 |
| WO | WO 99/03404 | 1/1999 |
| WO | WO 99/05977 | 2/1999 |
| WO | WO 99/30640 | 6/1999 |
| WO | WO 99/39649 | 8/1999 |
| WO | WO 99/42059 | 8/1999 |
| WO | WO/00/27292 | 2/2000 |
| WO | WO 01/15608 A1 | 3/2001 |
| WO | WO 02/02018 A1 | 1/2002 |

* cited by examiner

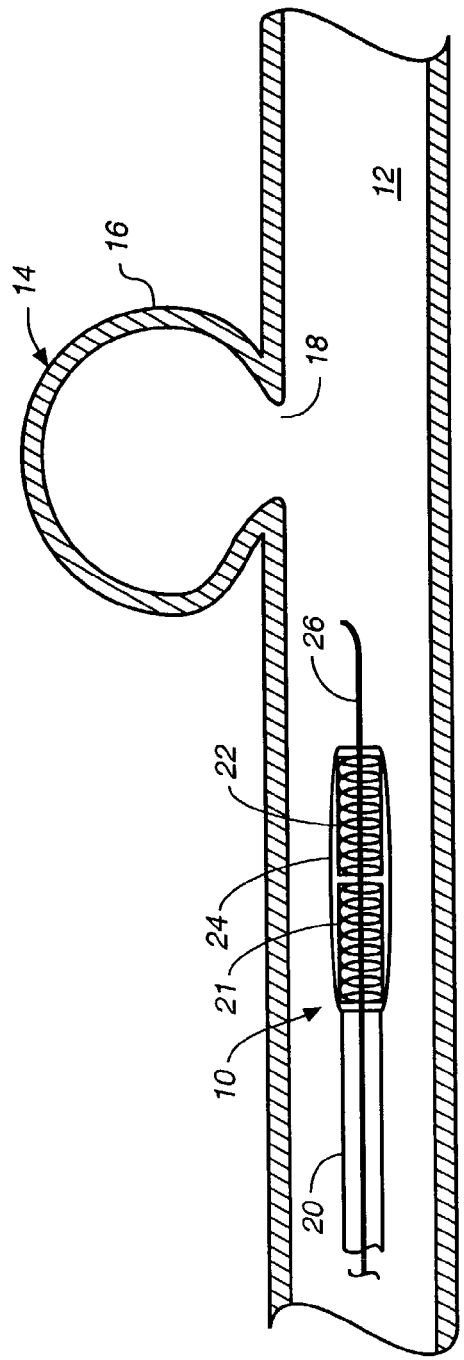
FIG._1A
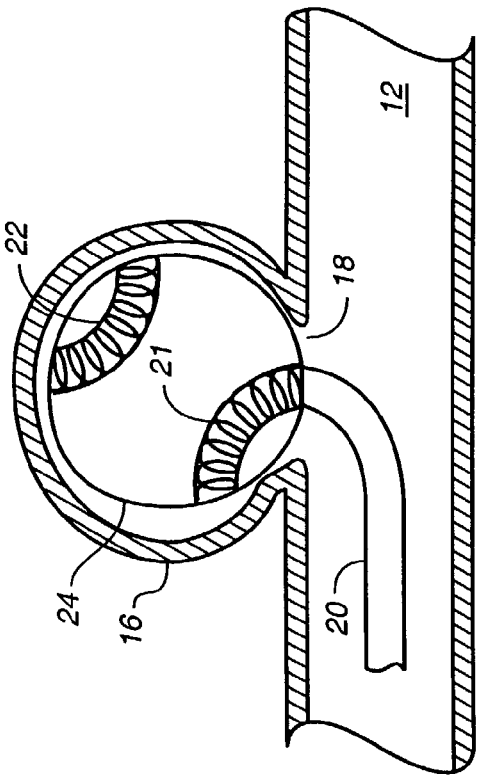
FIG._1C
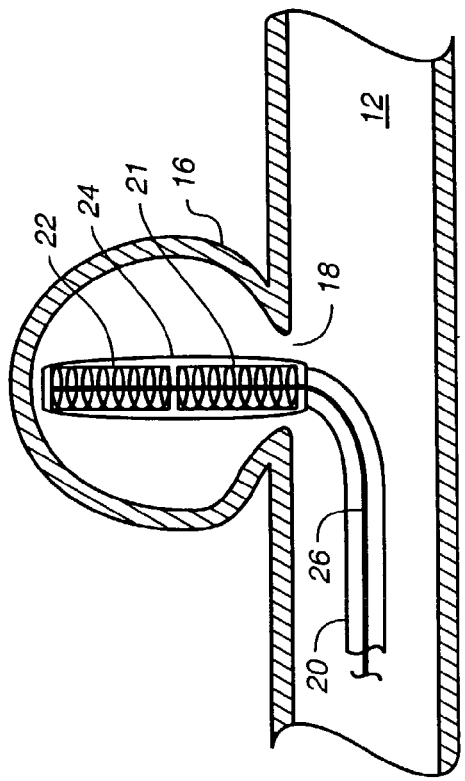
FIG._1B

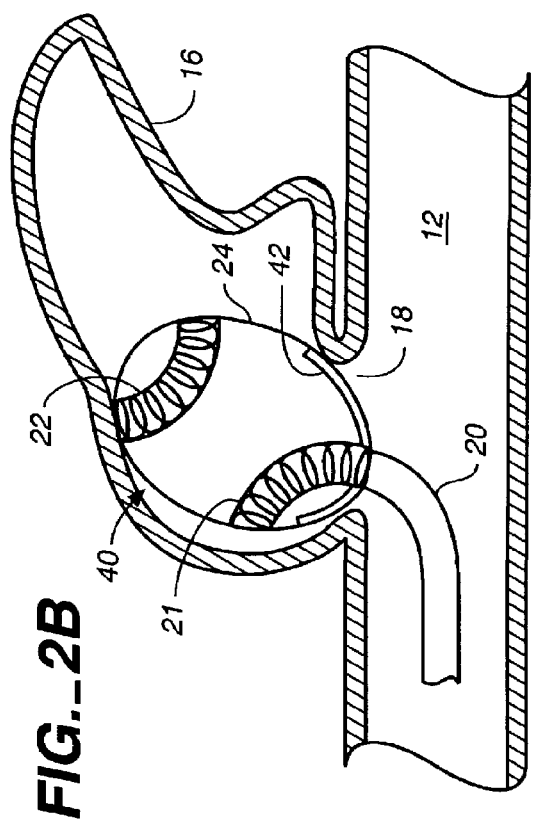
*FIG._2B*
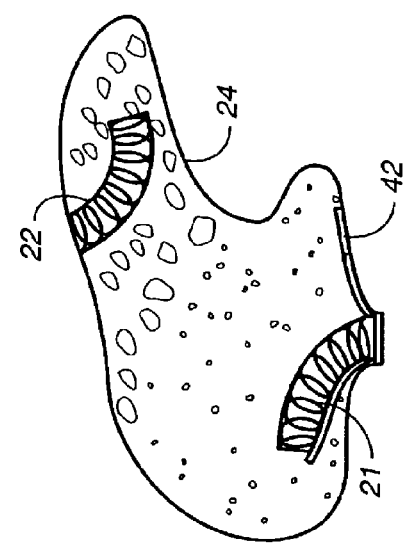
*FIG._2D*
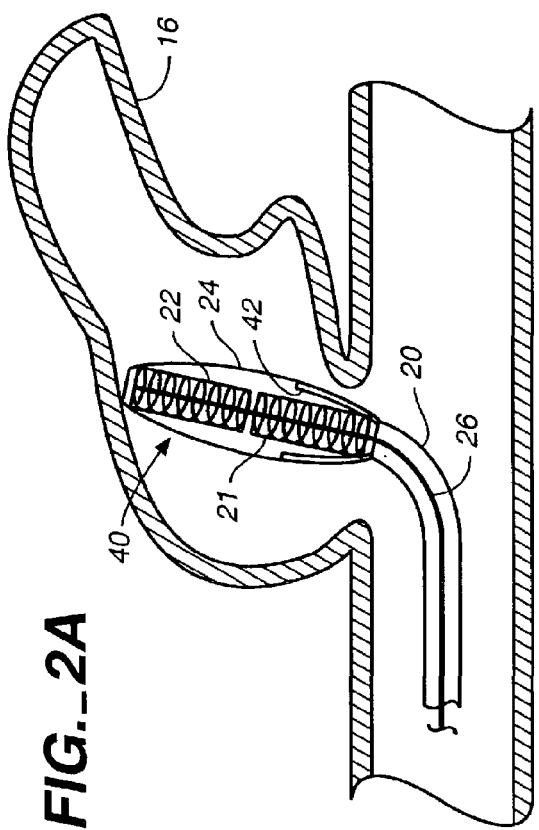
*FIG._2A*
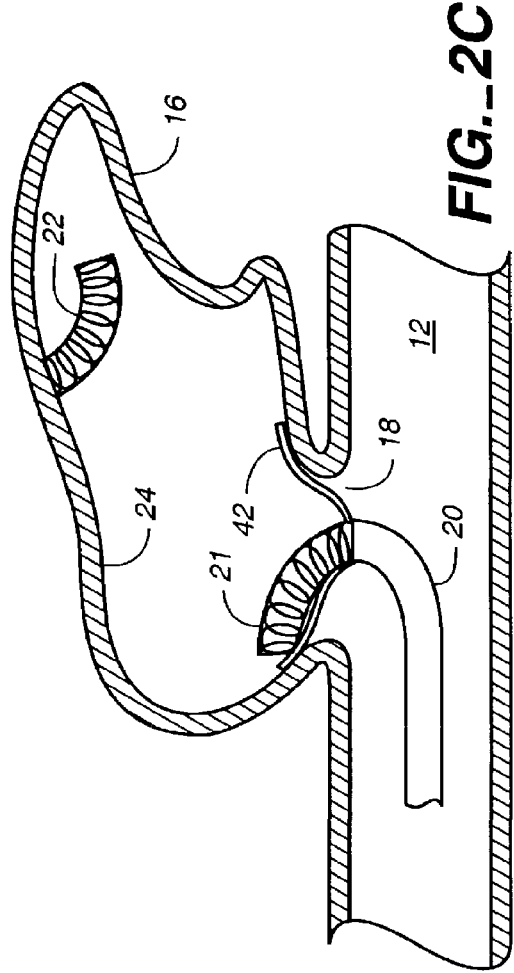
*FIG._2C*

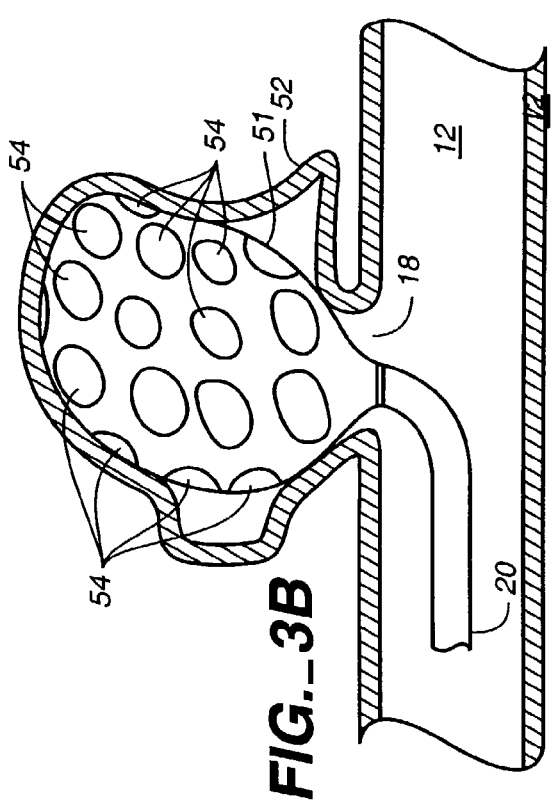
FIG._3A
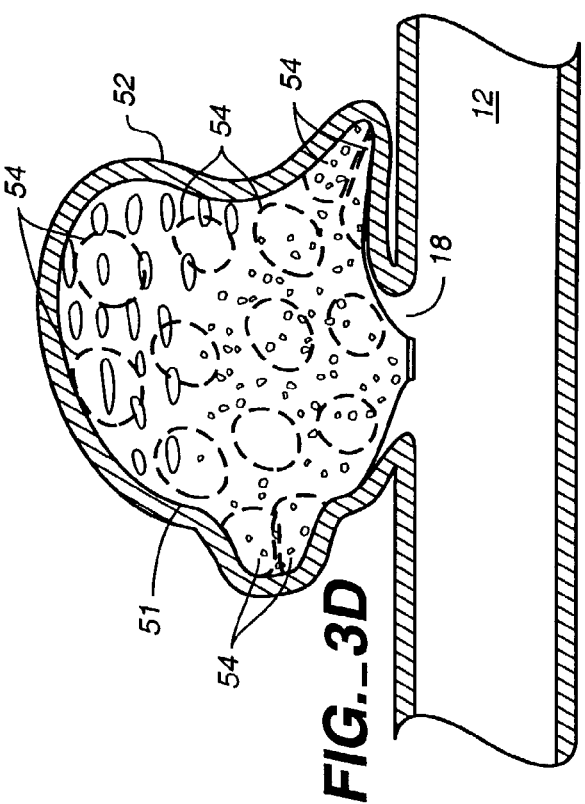
FIG._3B
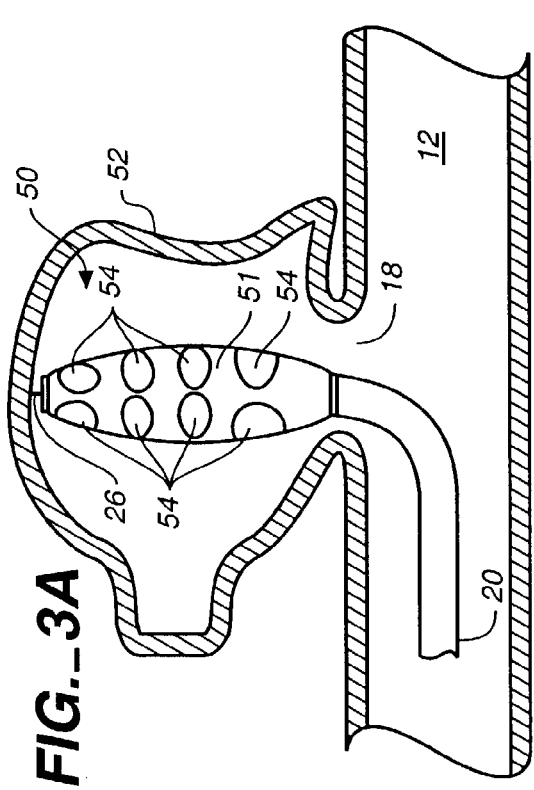
FIG._3C
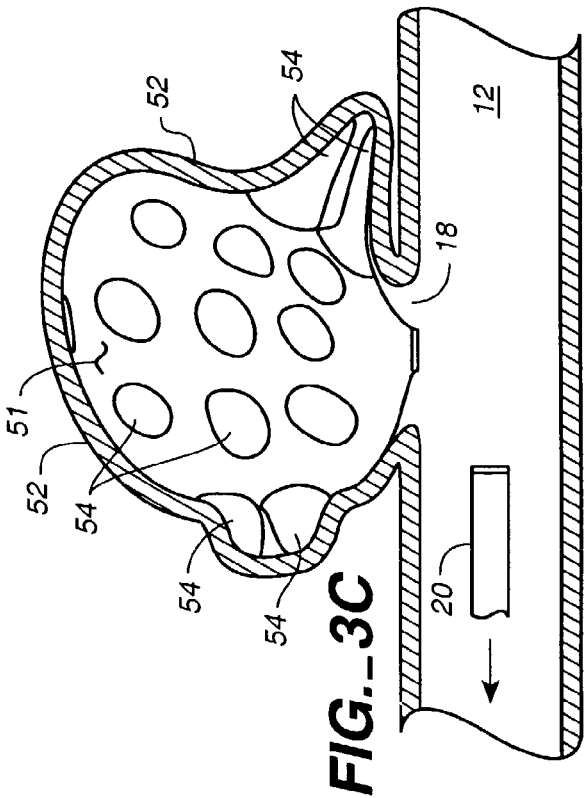
FIG._3D

EXPANDABLE BODY CAVITY LINER DEVICE

BACKGROUND OF THE INVENTION

The present invention deals with a system for treating a vascular cavity. More specifically, the present invention is directed to vascular cavity liners and vascular cavity neck bridges.

While the present discussion proceeds with respect to aneurysms, it will be appreciated that it can be applied to other vascular cavities (such as vessels, lumens, etc.) as well. An aneurysm or vascular malformation is a localized stretching or distension of an artery due to a weakening of the vessel wall. For example, "berry" aneurysms, i.e., small spherical distensions, occur in the vessels of the brain. The distension—often referred to as the aneurysm sac—is related to defects in the muscular coating of the artery and is probably degenerative in origin. Rupture of aneurysms account for the majority of spontaneous hemorrhages. Approximately 25,000 intracranial aneurysms rupture every year in North America.

Several methods of treating aneurysms have been attempted, with varying degrees of success. At present, the treatment of aneurysms with drugs is substantially ineffective. Also, extra-vascular surgery, referred to as open craniotomy, for the purpose of preserving the parent artery is replete with disadvantages. A patient subject to open craniotomy for intercranial aneurysms typically must undergo general anesthesia, surgical removal of part of the skull, brain retraction, dissection around the neck of the sac, and placement of a clip on the parent artery to prevent bleeding or rebleeding.

Alternative treatments include endovascular occlusion where the interior of the aneurysm is entered with a guidewire or a microcatheter. An occlusion is formed within the sac with an intention to preserve the parent artery. One means for forming a mass is through the introduction of an embolic agent within the sac. Examples of embolic agents include a detachable coil, which is detached from the end of a guidewire, a liquid polymer which polymerizes rapidly on contact with blood to form a firm mass, and embolic particles.

Endovascular occlusion is not without drawbacks. For example, there is a risk of overfilling the sac and consequent embolic agent migration into the parent vessel. Overfilling of the sac also generates additional pressure in the aneurysm.

Another means for forming a mass in the aneurysm sac involves the placement of an elastic, expandable balloon or liner in the aneurysm. Detachable occlusion balloons have been used for a number of medical procedures. These balloons are carried at the end of a catheter and, once inflated can be detached from the catheter. Such a balloon may be positioned within an aneurysm, filled and then detached from the catheter. Deploying the balloon within the aneurysm can be rather difficult due to the high rates of blood flow through the aneurysm. Elastic balloons have exhibited problems with respect to performance and have not been used endovascularly in some time.

This aneurysm filling technique also has its problems. As the balloon is filled, the operator must be very careful not to overfill the balloon due to possible risk of rupturing the aneurysm. Accordingly, the balloon may be too small, potentially resulting in the release of the balloon from the aneurysm into the blood stream. Furthermore, the balloon often does not mold or shape to the odd-shaped contours of the aneurysm leaving room for blood to continue flowing through the aneurysm, or generating undesired pressure on the aneurysm wall.

Aneurysm liners are composed of a liner sac which is placed in the aneurysm and filled to occlude the aneurysm. A guidewire is inserted in the liner. The guidewire carries the liner through the vasculature to deploy the liner in the aneurysm.

All of the present systems for treating aneurysms have disadvantages as well. For example, while the aneurysm liner concept is intuitively attractive, it has posed a number of technical challenges. One primary challenge involves the difficulty in producing a material that is robust enough to contain embolic material without inhibiting the ability of the embolics to conform to the aneurysm geometry itself, rather than the geometry of the liner. For example, the elastic materials discussed above generally require to much force to deform, and inelastic materials that deform readily do not have adequate memory to conform to the aneurysmal wall.

Different types of aneurysms also present different challenges. For example, aneurysms which have a particularly wide opening between the aneurysm sac and the parent vessel ("wide neck aneurysms") present difficulties concerning the retention of embolic materials. Specifically, wide neck aneurysms make if very difficult to maintain the embolics, or occlusive materials, within the aneurysmal sac. This is especially true of liquid embolic materials. Of course, should the embolic material enter the parent vessel, it poses an undesirable risk of occlusion in the parent vessel.

Some current aneurysm liner concepts are inadequate in treating larger aneurysms. For example, some liner concepts involve forming the aneurysm liner of a woven or braided polymeric material such as polypropylene, polyester, nylon, urethane, teflon, etc. However, these mesh materials are difficult to use in treating aneurysms larger than, for example, twelve millimeters in diameter. Such mesh materials result in an assembly which is too bulky when collapsed down onto the catheter for delivery. In other words, the amount of materials required to fill a relatively large aneurysm is very difficult to collapse down into a constrained, low profile, delivery configuration small enough to be delivered and deployed without excess friction on the walls of the delivery catheter or other delivery lumen.

SUMMARY OF THE INVENTION

The present invention is a vascular cavity treatment device for treating vascular cavities of various shapes and sizes and will be discussed by way of example as an aneurysm treatment device.

In one embodiment, the aneurysm treatment device includes an aneurysm liner formed of material having very low yield strength and very low elasticity so that, with a relatively low amount of internal pressure exerted by, for example, embolic material, the aneurysm liner readily plastically deforms to the internal geometry of the aneurysm sac. A second, reinforcing layer is deployed on the first material. The reinforcing layer is more elastic than the first material and has a much higher yield strength. The reinforcing layer is illustratively disposed at the neck of the aneurysm liner device.

BRIEF DESCRIPTION OF THE DRAWINGS

FIGS. 1A-1C illustrate the deployment of an aneurysm liner in an aneurysm.

FIGS. 2A-2C illustrate an embodiment of an aneurysm liner being formed of materials with two different characteristics, one of them having a very low yield strength and the other having a high yield strength and a greater elasticity.

FIG. 2D illustrates the embodiment shown in FIGS. 2A-2C, with perforations therein.

FIGS. 3A-3C illustrate an embodiment of an aneurysm liner being formed of a balloon material having two different characteristics, portions thereof being weaker than other portions thereof.

FIG. 3D illustrates the embodiment shown in FIGS. 3A-3C with perforations therein.

DETAILED DESCRIPTION OF THE ILLUSTRATIVE EMBODIMENTS

FIGS. 1A-1C illustrate a portion of an aneurysm treatment device 10 in a vessel 12 which has an aneurysm 14 therein, and thus illustrate the general context of the present invention. Though the embodiments discussed herein are discussed in conjunction with an aneurysm, it will be appreciated that they can be used in substantially any vascular cavity or other bodily cavities. Aneurysm 14 is defined by aneurysmal sac 16 and neck 18. Device 10 includes, in the embodiment illustrated, delivery catheter 18, a pair of extender coils 21 and 22 and an expandable liner (aneurysm liner sac) 24. Delivery catheter 20 has a proximal end that extends proximally to a position where it is manipulable by an operator. The distal end of catheter 20 is releaseably connected to the liner 24 and coil 21. Coils 21 and 22 can either be attached to the liner or catheter, or unattached. In addition, there can also be one or more coils disposed between coils 21 and 22 and axially aligned therewith.

When in the insertion position shown in FIG. 1A, coils 21 and 22 (and other optional coils therebetween) are axially aligned with one another, their length is sufficient to substantially hold liner 24 in a low profile position for insertion and manipulation within the vasculature. In one embodiment, coils 21 and 22 are axially aligned with one another and with catheter 20 through the use of a guidewire 26 which is disposed within the lumen of catheter 20, through coils 21 and 22 and liner 24, and out the distal end of catheter 22 and liner 24. Coils 21 and 22 are held in an axially aligned conformation by guidewire 26 such that coils 21 and 22 substantially conform to the curvature of guidewire 26. Coils 21 and 22, rather than guidewire 26, can act to extend and even tension liner 24.

FIG. 1B shows that treatment device 10 has been positioned through vessel 12 and neck 18 into the sac 16 of aneurysm 14. Similar items are similarly numbered to those shown in FIG. 1A. In use, aneurysm treatment device 10 can be preloaded or back loaded onto guidewire 26. Guidewire 26 is manipulated through the vasculature from the entry site (such as the femoral artery) to the region of vessel 12 containing the aneurysm. The distal tip of guidewire 26 is advanced across the neck 18 of aneurysm 14 and into the aneurysm sac 16. This can be done using any desirable visualization technique. In one embodiment, catheter 20 is placed over guidewire 26 prior to positioning guidewire 26 in the vasculature, with several centimeters of guidewire 26 extending distal of the distal tip of catheter 20. Therefore, when the distal end of guidewire 26 has passed the aneurysm neck 18, catheter 20 is positioned just proximal of neck 18. Treatment device 10 is then advanced into the aneurysm sac 16.

In another embodiment, guidewire 26 is placed in the vasculature first. Once the distal end of guidewire 26 is moved past the aneurysm neck 18, into the aneurysm sac 16, catheter 20 is advanced over guidewire 26 such that the extender coils 21 and 22 are pushed distally along the guidewire by the catheter 20 until the aneurysm treatment device 10 is in place in the aneurysm sac 16.

FIG. 1C illustrates treatment device 10 deployed in aneurysm sac 16 in accordance with one embodiment. Similar items are similarly numbered to those shown in FIGS. 1A and 1B. Once device 10 is substantially fully within aneurysm sac 16, guidewire 26 is retracted proximally, but liner 24 remains connected to delivery catheter 20. The distal end of delivery catheter 20 holds expandable liner 24 in position within the aneurysm sac 16 while expandable liner 24 is filled with embolics. Expansion of liner 24 occurs after the distal end of guidewire 26 is retracted from the coils 21 and 22.

As shown in FIG. 1C, once guidewire 26 has been retracted, coils 21 and 22 recoil away from axial alignment with one another toward the periphery of liner 24. In one illustrative embodiment, coils 21 and 22 are biased to extend in opposite directions to enhance deployment of, and expansion of, liner 24 within aneurysm sac 16. If any coils are disposed between coils 21 and 22 on guidewire 26, they simply fall away and float within liner 24. Embolic material can now be introduced into liner 24 through catheter 20 using substantially any desired method. Such methods include, for example, advancing coils or particles into liner 24, pushing the embolic material into catheter 20 with guidewire 26 completely removed, or infusing or injecting embolic material through catheter 20 into liner 24. Liner 24 is thus filled with a common embolic agent, such as detachable coils, particles, acrylics, hydrogel, etc.

Once liner 24 is filled, it is unable to be removed through aneurysm neck 18. Therefore, it is released from delivery catheter 20 and delivery catheter 20 is removed from the treatment site. Detachment of liner 24 from catheter 20 can be accomplished using any desired method, such as using electrolytic detachment, traction-based detachment, or other mechanical, electrical, heat-based, magnetic, chemical or other detachment.

FIGS. 1A-1C illustrate that device 10 is configured for convenient treatment of aneurysm 14, and in particular, a generally symmetrically shaped aneurysm. However, asymmetrically shaped aneurysm sacs, or those having an otherwise irregular geometrical shape present other problems. For example, if aneurysm sac 16 had a cavity extending out one side thereof, it may be difficult for liner 24 to fill that portion of the aneurysm sac.

FIGS. 2A and 2B illustrate yet another embodiment of an aneurysm treatment device 40 in accordance with another embodiment of the present invention. Aneurysm treatment device 40 is similar, in many ways, to the previous embodiments, in that it can illustratively include interior extender coils 21 and 22 (and optional coils therebetween) and can be positioned over a guidewire 26 using a detachable delivery catheter 20. Treatment device 40 also illustratively includes a liner 24.

However, treatment device 40 also includes other or different features. FIG. 2A shows treatment device 40 having already been positioned within an asymmetrical aneurysm sac 16, which has a highly irregular geometry. FIG. 2A shows that treatment device 40 not only includes liner (first portion) 24, but also illustratively includes a reinforcing layer (or second portion) 42. Liner 24 and layer 42 are described in greater detail below.

FIG. 2B shows partial deployment of aneurysm liner 24 after guidewire 26 has been removed and extender coils 21 and 22 fall away from axial alignment with one another. Liner 24 is also at least partially expanded to the position shown in FIG. 2B through the introduction of embolic material therein to slightly elevate the internal pressure in liner 24 above ambient (e.g., 0-1 ATM), using catheter 20.

In accordance with one embodiment of the present invention, liner 24 is illustratively formed of a polymer that has a very low yield strength and a low elasticity so that, with a minimal amount of additional force exerted by the embolic material (e.g., 0-5 ATM and illustratively 0-2 ATM or 1-2 ATM), the polymer material forming liner 24 readily plastically expands to conform to the interior perimeter of aneurysmal sac 16. This is illustrated in FIG. 2C. In other words, liner 24 is formed of a polymer having characteristics such that by the continued introduction of embolic material into liner 24, liner 24 simply permanently deforms to assume the shape of the aneurysm sac 16. The material which forms liner 24 also has sufficient ultimate failure strength so as not to tear during delivery or expansion thereof.

In addition, reinforcement layer 42 is more elastic and of a much higher yield strength. Reinforcement layer 42 is illustratively located in the region of aneurysm liner 24 close to its attachment point to catheter 20 (neck portion). This ensures that it will be located preferentially near aneurysm neck 18 in order to prevent aneurysm liner 24 from expanding through neck 18, and into parent vessel 12. Thus, the distal end of treatment device 40 can easily expand into the irregular geometrical portions of the aneurysmal sac, while the proximal portion thereof does not deform as easily and thus prevents deformation into parent vessel 12. Reinforcement layer 42 can also be discontinuous or formed of a braid or mesh or polymer material or other reinforcing material and can be radiopaque as well.

FIG. 2D shows another embodiment of treatment device 40 with perforations formed therein. These perforations allow blood to escape from the aneurysmal sac, through liner 24, and reinforcing layer 42, into the parent vessel 12, as liner 24 is expanded. However, as with the previous embodiments, the perforations are not necessary and the blood can simply escape around the outside of device 40 and through neck 18. Also, the perforations are shown as being larger distally, to allow distal permeation of embolics, although this is optional as well.

For example, spherical PVA embolics may traditionally be 500 microns in size and may be used to fill a conventional aneurysm liner. The distal portion of device 40 can thus be perforated with 750 micron holes whereas the proximal portion near the neck 18 of aneurysm sac 16 can illustratively be perforated with 350 micron sized, irregularly distributed, holes. Therefore, as the embolics are introduced into liner portion 24, they are sized to be able to escape the distal end thereof and or occupy the irregular spaces in the aneurysm sac 16, without escaping back into the parent vessel 12.

FIGS. 3A-3C illustrate another embodiment of an aneurysm treatment device 50 in accordance with one aspect of the present invention. Similar items are similarly numbered to those shown in previous Figures. Treatment device 50 is similar, in many ways, to the previous embodiments in that it can illustratively include interior extender coils 21 and 22 (and optional coils therebetween) and can be positioned over a guidewire 26 using a detachable delivery catheter 20. Treatment device 50 also illustratively includes a liner 51.

However, treatment device 50 also illustratively includes other or different features. FIG. 3A shows treatment device 50 having already been positioned within an asymmetrical aneurysm sac 52, which has a highly irregular geometry.

In the embodiment shown in FIG. 3A, liner 51 is illustratively formed as a detachable balloon. The balloon material illustratively has a plurality of areas 54 disposed on its surface which are weaker (or more elastic) than the remainder of the surface of liner 51. In one illustrative embodiment, areas 54 are simply formed of thinner balloon material than the remainder of liner 51. Of course, they could be formed of different, more elastic (or weaker) material, or the remainder of liner 51 (other than areas 54) can be enclosed in a braid, a mesh, a polymer material or otherwise coated with a material which precludes that portion of liner 51 from expanding beyond a predetermined geometry and may be radiopaque as well.

FIG. 3B illustrates aneurysm treatment device 50 expanded under a first predetermined pressure. In one illustrative embodiment, liner 51 is inflated with a contrast medium, or saline solution, or another fluid introduced through catheter 20. As the pressure in liner 51 increases, liner 51 inflates to a first predetermined dimension in which areas 54 are not expanded beyond the remainder of liner 51.

FIG. 3C illustrates liner 51, after it has been subjected to additional internal pressure. It can be seen that liner 51 has now assumed an irregular shape because the weaker regions 54 have expanded to fill void spaces of aneurysm sac 52. This allows liner 51 to substantially fill even irregularly shaped aneurysm sac 52. FIG. 3C also illustrates that, in a region of liner 51 proximate neck 18 of the aneurysm there are no weak zones 54. This helps to preclude any portion of the aneurysm liner 51 from expanding into parent vessel 12, and thereby fully or partially occluding the vessel.

It should also be noted that, in one illustrative embodiment, liner 51 need not even substantially fill the entire aneurysm sac 52. Instead, liner 51 can simply be inflated to a geometry in which enough of the weaker regions 54 have been expanded into void spaces or lobes of aneurysm sac 52 to securely anchor liner 51 within aneurysm sac 52 and to block the inflow zone through neck 18. In that embodiment, even if the entire aneurysm sac 52 is not filled, the neck 18 is blocked and device 50 is anchored in place to inhibit further growth of the aneurysm.

In another illustrative embodiment, aneurysm liner 51 can be filled with embolics or other polymeric materials, or coils. This may enhance the long term stability of liner 51 within aneurysm sac 52.

FIG. 3D is another illustrative embodiment of the present invention. FIG. 3D is similar to the embodiment illustrated in FIGS. 3A-3C, except that it has perforations therein. Weak regions 54 are illustrated by dashed lines while the perforations are illustrated by either points or circular or oval shaped regions. The perforations allow introduced embolic material to seek out the void spaces, or irregular lobes, of aneurysm sac 52. The perforations also allow blood that is being displaced in aneurysm sac 52 to re-enter parent vessel 12 through aneurysm liner 51. Further, the embodiment in FIG. 3D shows that the perforations can be formed to preferentially permeate embolics distally. In other words, the distal perforations are larger than the proximal perforations such that embolics can permeate the distal perforations but not the proximal perforations. However, the presence of the perforations are optional, as is the sizing of any perforations which may be used.

Further, weak regions can be other shapes as well, such as annular rings around liner 51, axial stripes or substantially any geometric shape.

It should further be noted that all of the embodiments discussed herein can optionally have biodegradable, cell growth enhancing material such as polyglycolic acid (PGA) or polylactic acid (PLA) disposed thereon in a region that will illustratively be deployed in a neck region of the aneurysm. Of course, other material or combinations of these materials may be used as well.

Also, the devices described herein can be releasably attached to guidewire 26 instead of the catheter.

It can thus be seen that the present invention provides a number of different embodiments for treating aneurysms. These embodiments address many of the various deficiencies and disadvantages associated with prior aneurysm treatment devices.

Although the present invention has been described with reference to illustrative embodiments, workers skilled in the art will recognize that changes may be made in form and detail without departing from the spirit and scope of the invention.

What is claimed is:

1. An aneurysm liner, comprising:
a liner sac disposable within an aneurysm and having an expandable body having an outer surface which faces the wall of an aneurysm when in place within the aneurysm and an inner surface, the body having a first portion and a second portion, said first portion having an exterior surface which forms a part of the outer surface of said body and said first portion having a first elasticity, said second portion having an exterior surface which forms a part of the outer surface of said body and said second portion having a second elasticity different from the first elasticity, wherein the first portion of the expandable body has a first yield strength and the second portion has a second yield strength.

2. The aneurysm liner of claim 1 wherein the first portion is expandable to a first configuration under a first internal pressure and plastically deforms to a second configuration under a second internal pressure, insufficient to plastically deform the second portion.

3. The aneurysm liner of claim 2 wherein the aneurysm liner sac assumes the second configuration under the second internal pressure in a range of 0-5 atmospheres.

4. The aneurysm liner of claim 2 wherein the second internal pressure is in a range of 0-2 atmospheres.

5. The aneurysm liner of claim 1 wherein the first and second portions are formed of first and second materials, respectively.

6. The aneurysm liner of claim 5 wherein the second portion comprises a braided, mesh or polymer material.

7. The aneurysm liner of claim 1 wherein the first and second portions are formed of a single material.

8. The aneurysm liner of claim 7 wherein the first and second portions have different thicknesses.

9. The aneurysm liner of claim 8 wherein the material comprises a balloon material.

10. The aneurysm liner of claim 9 wherein the liner sac expands to a first configuration under a first internal pressure and wherein the first portion preferentially expands under a second, elevated, internal pressure.

11. The aneurysm liner of claim 10 wherein a region of the liner sac proximate a neck of the aneurysm is formed of the second portion.

12. The aneurysm liner of claim 1 wherein the liner sac is configured to be detachably connected to a delivery catheter.

13. The aneurysm liner of claim 1 wherein the liner sac is configured to be detachably connected to a guidewire.

14. The aneurysm liner of claim 1, wherein the first portion comprises a plurality of regions spaced from each other.

15. The aneurysm liner of claim 14, wherein the second portion comprises a plurality of spaced apertures, and the regions of the first portion are located adjacent to the respective apertures of the second portion.

16. The aneurysm liner of claim 15, wherein the regions of the first portion protrude through the respective apertures of the second portion under internal pressure.

17. The aneurysm liner of claim 1, wherein the body has a plurality of perforations.

18. The aneurysm liner of claim 1, wherein the second portion has a reinforcement that contributes to the second elasticity of the second portion.

19. The aneurysm liner of claim 1, wherein the second portion comprises a coating that contributes to the second elasticity of the second portion.

20. The aneurysm liner of claim 1, wherein the first and the second portions each comprises a surface of the liner sac.

21. An aneurysm liner, comprising:
a liner sac disposable within an aneurysm and having an expandable body having an outer surface which faces the wall of an aneurysm when in place within the aneurysm and an inner surface and an internal surface, the body having a first portion and a second portion, said first portion having an exterior surface which forms a part of the outer surface of said body and said first portion expandable to a first configuration under a first internal pressure, said second portion having an exterior surface which forms a part of the outer surface of said body and said second portion being configured such that it plastically expands to a second configuration under a second, higher internal pressure, wherein the second internal pressure is insufficient to plastically deform the first portion.

22. The aneurysm liner of claim 21, wherein the body comprises a plurality of perforations.

23. The aneurysm liner of claim 22, the perforations have different sizes.

24. The aneurysm liner of claim 21, wherein the first portion has a first elasticity, and the second portion has a second elasticity different from the first elasticity.

* * * * *